United States Patent [19]

Willert

[11] Patent Number: 5,019,106
[45] Date of Patent: May 28, 1991

[54] FIXING STEM FOR A PROSTHESIS

[75] Inventor: Hans-Georg Willert, Göttingen, Fed. Rep. of Germany

[73] Assignee: Sulzer Brothers Limited, Winterthur, Switzerland

[21] Appl. No.: 392,771

[22] Filed: Aug. 11, 1989

[30] Foreign Application Priority Data

Aug. 15, 1988 [CH] Switzerland .................. 3061/88

[51] Int. Cl.⁵ ............................................. A61F 2/32
[52] U.S. Cl. ..................................................... 623/22
[58] Field of Search ................................. 623/22, 23

[56] References Cited

U.S. PATENT DOCUMENTS

| 3,067,740 | 12/1962 | Haboush | 623/23 |
| 3,320,951 | 5/1967 | Wittebol | 623/23 |
| 4,287,617 | 9/1981 | Tornier | 623/23 |
| 4,516,277 | 5/1985 | Butel | 623/23 |
| 4,671,275 | 6/1987 | Deyerle | 623/23 |
| 4,808,186 | 2/1989 | Smith | 623/23 |
| 4,840,633 | 6/1989 | Kallabis et al. | 623/23 |

FOREIGN PATENT DOCUMENTS

| 0190446 | 8/1986 | European Pat. Off. . | |
| 0244720 | 11/1987 | European Pat. Off. | 623/23 |
| 2933271 | 3/1981 | Fed. Rep. of Germany . | |
| 2289163 | 5/1976 | France . | |
| 2549717 | 2/1985 | France | 623/22 |
| 2591885 | 6/1987 | France . | |

Primary Examiner—Randall L. Green
Assistant Examiner—David H. Willse
Attorney, Agent, or Firm—Kenyon & Kenyon

[57] ABSTRACT

The distal region of the fixing stem of the femur head prosthesis is formed with an elongated slot to increase resilience. The slot is closed at the distal end by a closure element which facilitates implanting of the stem without destroying the increased resilience.

7 Claims, 1 Drawing Sheet

FIXING STEM FOR A PROSTHESIS

This invention relates to a fixing stem for a prosthesis. More particularly, this invention relates to a fixing stem for a cementless fixing of a femoral head prosthesis in a femur bone cavity.

As is known, femoral prosthesis have been constructed in various fashions for purposes of manufacturing or for purposes of implantation. For example, European patent application Ser. No. 0190446 describes a hollow femur prosthesis whereas German O.S. No. 2933271 describes a prosthesis having a hollowed shank. In other cases, it has been known to provide the stem of a prosthesis with elongated slots, for example as described in French Patent No. 2,289,163.

Still further, it has been known, for example, from French Patent No. 2591885, German Patent No. 3443304 and European patent application No. 0222336 to form a prosthesis with a slotted stem or with cavities or slots in the stem in order to reduce the pressure exerted by the stem during implantation on the inner wall of an operatively prepared femur bone cavity However, it has been found that with stems that are "open" in the distal region that there is a risk of the prosthesis becoming stuck upon being introduced into the bone cavity. It has also been found that the resilience of the stem may, in some circumstances, be excessive particularly at the open end. This, in turn, leads to relative movements between the stem and the bone and to reduced torsional stability of the stem.

Accordingly, it is an object of the invention to provide a fixing stem for a prosthesis which has sufficient resilience to permit implantation without excessive stressing while at the same time precluding the stem from becoming stuck during implantation.

It is another object of the invention to improve the ability of a prosthesis stem to be removed from a bone cavity during re-operation.

It is another object of the invention to preclude the sticking of a prosthesis stem having a hollowed distal region in a femur bone cavity.

Briefly, the invention provides a fixing stem for a femoral head prosthesis which has a hollowed distal region with resilient walls to impart a degree of resilience to the stem for implanting in a femur bone cavity without excessive stressing and a closure element bridging the walls at a distal end thereof to preclude the stem from becoming stuck during implantation.

The stem is constructed such that the walls define an elongated slot which may decrease in width between the walls in a distal direction.

The distally closed slot, in similar manner to an open slot, permits a grading of the pressure exerted by the stem. Consequently, gradual transitions for the introduction of forces into the bone can be contrived and excess stressing obviated. The decreasing width of the slot from a proximal region towards the distal region provides a means of controlling the resilience of the stem.

The distal closure of the slot also facilitates limiting the resilience of the stem at the distal end so that torsional stability is not impaired. The distal closure also precludes the risk of the stem becoming stuck during implantation.

The closed slot may also be effective as a receptacle for at least one pharmaceutical ingredient. Further, if the slot remains open laterally so that tissue may grow through the slot, re-operations may, in some circumstances, be facilitated if a cutting edge extends along each wall and the closure element about a distal end of the slot. In such cases, the cutting edges serve to sever the invading tissue during withdrawal of the stem from a femur bone.

A plastic filling member may also be introduced into the slot or the slot may be closed by, for example sheet metal members.

These and other objects and advantages of the invention will become more apparent from the following detailed description taken in conjunction with the accompanying drawings wherein:

FIG. 2 illustrates a view taken on line II—II of FIG. 1;

Figure 1:
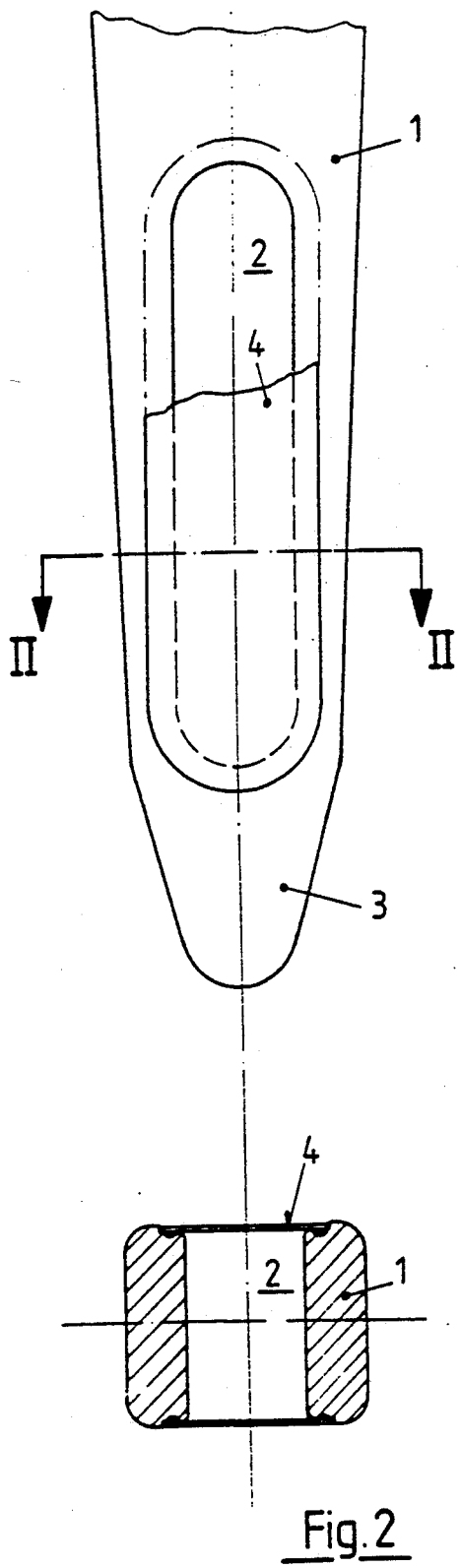
FIG. 1 illustrates a distal end of a straight stem of a femoral head prosthesis constructed in accordance with the invention.

Referring to FIG. 1, the fixing stem 1 for a femoral head prosthesis is made of metal and narrows conically on all sides in the distal direction. As indicated in FIG. 2, the stem 1 has a rectangular cross-section and has a hollowed distal region defining an elongated slot 2. The walls of the stem which define the slot are such as to impart a degree of resilience to the stem 1 for implanting in a femur bone cavity without excessive stressing.

As shown in FIG. 1, the hollowed distal region has a closure element 3 which bridges the walls at a distal end thereof to close off the slot 2 and which is an integral part of the stem 1. This closure element 3 serves to preclude the stem 1 from becoming stuck during implantation. That is, the conically shaped closure element 3 does not provide a bifurcated end as in the case of an open stem which might otherwise hang-up on a wall of a femur bone cavity.

The slot 2 may be filled with a plastic filling member (not shown) in order to inhibit invasion of tissue. Alternatively, the slot 2 may be used as a cavity to receive at least one pharmaceutical substance, for example as described in European patent application No. 0244720. In this respect, any suitable type of medicament may be stored within the slot 2. Advantageously, in this case, the slot 2 is closed by a pair of porous covers 4 which are mounted on the walls of the slot 2 in order to contain the substance therein while also preventing invasion of tissue after the pharmaceutical substance has dissolved out of the slot 2.

Figure 3:
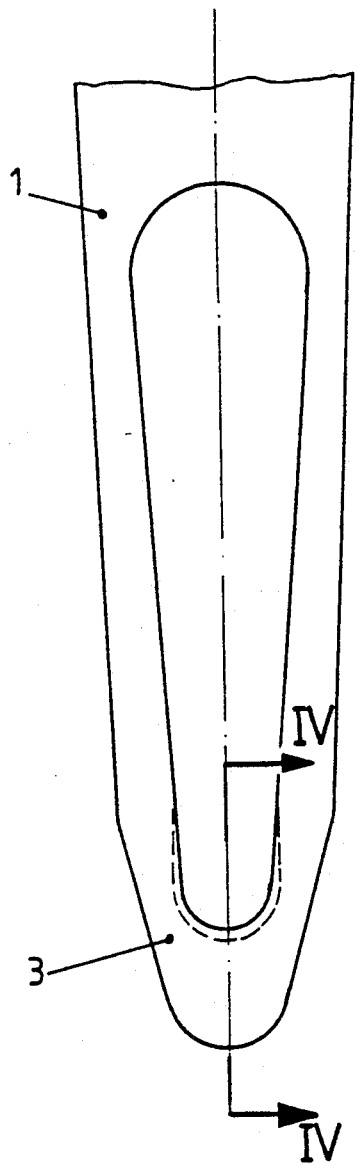
FIG. 3 illustrates a modified stem having an elongated slot of decreasing width in accordance with the invention.
Figure 4:
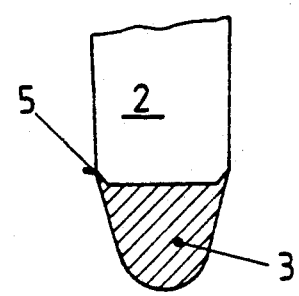
FIG. 4 illustrates a view taken on line IV—IV of FIG. 3.

Referring to FIG. 3, the slot 2 may be of decreasing width between the walls in the distal direction in accordance with the conical narrowing of the stem 1.

When the slot 2 is open laterally, in order to facilitate re-operations, a cutting edge 5 extends along each wall and the closure element 3 about the distal end of the slot 2. These cutting edges 5 serve to sever invading tissue upon withdrawal of the stem 1 from a femur bone.

The invention thus provides a fixing stem for a femoral head prosthesis which has a hollowed region which retains sufficient resilience to avoid excessive stressing when implanting the stem in a bone cavity. At the same time, the closure element and the distal end of the stem precludes the stem from becoming stuck in the bone cavity. Also, the closure element serves to limit the resilience of the stem at the distal end so that torsional stability is not impaired.

What is claimed is:

1. A fixing stem for a femoral head prosthesis having a main body portion, a hollowed distal region having a pair of resilient walls extending distally from said body portion and defining a continuous outer surface with said body portion, an elongated slot between said walls extending in an anterior/posterior direction and a cutting edge on each wall about a distal end of said slot for severing invading tissue upon withdrawal of said stem from a femur, and a closure element bridging said walls at a distal end thereof to close said slot and the distal end of said distal region.

2. A fixing stem as set forth in claim 1 wherein said slot is of decreasing width between said walls in a distal direction.

3. A fixing stem as set forth in claim 1 which further comprises a pair of porous covers mounted between said walls to contain at least one pharmaceutical substance therein.

4. A fixing stem as set forth in claim 1 which further comprises a plastic filling member is disposed in said slot.

5. A fixing stem as set forth in claim 1 which further comprises a pair of porous covers mounted on said walls over said slot to contain a pharmaceutical substance therein.

6. A fixing stem for a femoral head prosthesis having a main body portion;
   a hollowed distal region extending from said body portion with resilient walls defining a continuous outer surface with said body portion and an elongated slot extending in an anterior/posterior direction between said walls to impart a degree of resilience to said stem for implanting in a femur bone cavity without excessive stressing,
   a closure element bridging said walls at a distal end thereof to close said hollowed distal region to preclude said stem from becoming stuck during implantation; and
   a cutting edge extending along each wall and said closure element about a distal end of said slot for severing invading tissue upon withdrawal of said stem from a femur bone.

7. A fixing stem as set forth in claim 6 wherein said slot is of decreasing width between said walls in a distal direction.

* * * * *

UNITED STATES PATENT AND TRADEMARK OFFICE
CERTIFICATE OF CORRECTION

PATENT NO. : 5,019,106
DATED : May 28, 1991
INVENTOR(S) : HANS-GEORG WILLERT

It is certified that error appears in the above-identified patent and that said Letters Patent is hereby corrected as shown below:

```
Column 1, line 11 change "patent application" to -Patent
     Application-

European"
Column 1, line 19 change "patent application" to -Patent
     Application-
Column 1, line 23 change "cavity However" to -cavity.  However- Column 2, line 46 change  "patent application" to -Patent
     Application-
```

Signed and Sealed this

Fifth Day of January, 1993

*Attest:*

DOUGLAS B. COMER

*Attesting Officer*       *Acting Commissioner of Patents and Trademarks*